United States Patent [19]

Köhler et al.

[11] Patent Number: 5,084,070
[45] Date of Patent: Jan. 28, 1992

[54] GUM-FREE COMPONENTS CONTAINING ALKYL TERT.-ALKYL ETHERS

[75] Inventors: Hans-Dieter Köhler; Bernhard Schleppinghoff, both of Dormagen; Bruno Schulwitz, Cologne; Hans-Volker Scheef; Herbert Tachorn, both of Dormagen, all of Fed. Rep. of Germany

[73] Assignee: Bayer Aktiengesellschaft, Leverkusen, Fed. Rep. of Germany

[21] Appl. No.: 638,138

[22] Filed: Jan. 7, 1991

Related U.S. Application Data

[63] Continuation of Ser. No. 96,707, Sep. 19, 1987, abandoned, which is a continuation of Ser. No. 836,050, Mar. 4, 1986, abandoned.

[30] Foreign Application Priority Data

Mar. 23, 1985 [DE] Fed. Rep. of Germany ....... 3510683
Oct. 30, 1985 [DE] Fed. Rep. of Germany ....... 3538564

[51] Int. Cl.$^5$ .................................................. C10L 1/18
[52] U.S. Cl. .......................................... 44/449; 44/447
[58] Field of Search ................................. 44/449, 447

[56] References Cited

U.S. PATENT DOCUMENTS

| | | | |
|---|---|---|---|
| 4,182,913 | 1/1980 | Takezono et al. | 44/56 X |
| 4,193,770 | 3/1980 | Chase et al. | 44/53 X |
| 4,330,679 | 5/1982 | Kohler et al. | 568/697 |
| 4,334,890 | 6/1982 | Kochar et al. | 44/53 |
| 4,361,422 | 11/1982 | Derrien et al. | 44/56 |

Primary Examiner—Prince Willis, Jr.
Assistant Examiner—Ellen McAvoy
Attorney, Agent, or Firm—Sprung, Horn, Kramer & Woods

[57] ABSTRACT

Gum-free fuel components containing alkyl tert.-alkyl ethers have been found which can be prepared by reacting a crude hydrocarbon mixture containing gum-forming constituents and containing one or more tert.-olefins, simultaneously with alkanols and $H_2$ on a certain exchanger in the $H^+$ form containing one or more metals of sub-group VI, VII or VIII of the periodic table of the element in element form, in the liquid phase at 30° to 140° C.

19 Claims, 1 Drawing Sheet

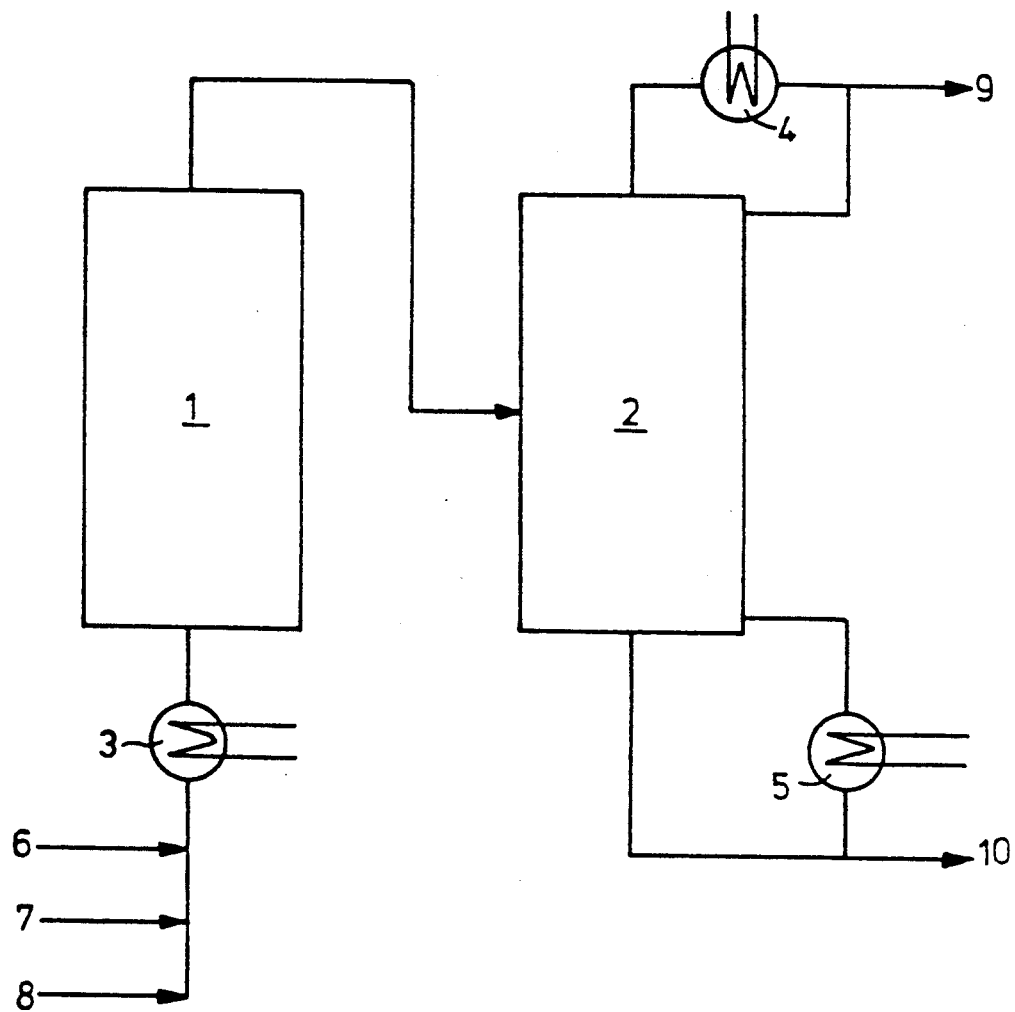

GUM-FREE COMPONENTS CONTAINING ALKYL TERT.-ALKYL ETHERS

This application is a continuation of application Ser. No. 096,707, filed 9/14/87, now abandoned, which is a continuation of Ser. No. 856,050 filed 3/4/86, now abandoned.

BACKGROUND OF THE INVENTION

The present invention relates to gum-free fuel components containing alkyl tert.-alkyl ethers which can be prepared from crude hydrocarbon mixtures containing tert.-olefins.

Gum in connection with fuels is understood as a content of oligomeric or polymeric substances in the fuel which manifests itself as the evaporation residue on analysis of the fuels. A gum content in the fuel leads to coking and deposits in the combustion chamber of the engine and is therefore extremely undesirable.

SUMMARY OF THE INVENTION

Gum-free fuel components containing alkyl tert.-alkyl ethers have now been found, which can be prepared by reacting a crude hydrocarbon mixture containing gum-forming constituents and containing one or more tert.-olefins, simultaneously with alkanols and hydrogen to form a reaction mixture, on a macroporous or gelatinous cation exchanger in the $H^+$ form containing 0.001 to 10 g of one or more metals of sub-group VI and/or VII and/or VIII of the periodic table of the elements in elemental form per liter of dry cation exchanger and with a degree of crosslinking of 2 to 65% and a specific surface area of 5 to 750 $m^2/g$ of dry exchanger resin, in the liquid phase at 30° to 140° C.

DETAILED DESCRIPTION OF THE INVENTION

Examples of tert.-olefines which may be mentioned are those which contain 5 to 8, preferably 5 to 7, C atoms; $C_5$- and/or $C_6$-tert.-olefines are particularly preferred. The crude hydrocabon mixtures to be employed according to the invention contain such tert.-olefines either essentially by themselves or as a mixture of several of them. For example, a hydrocarbon mixture essentially containing tert.-amylenes in general contains small amounts of i-butenes and/or tert.-hexenes.

The crude hydrocarbon mixtures to be employed according to the invention also contain, in addition to the tert.-olefines described, straight-chain and/or branched and/or cyclic saturated and monounsaturated hydrocarbons with essentially 5 to 8 C atoms and small amounts of the adjacent homologs, for example small amounts of $C_4$-hydrocarbons. Such crude hydrocarbon mixtures furthermore contain constituents which form oligomeric or polymeric substances, known to expert as "gum" under the reaction conditions. These gum-forming constituents are, for example, diolefines and/or acetylene compounds. In the case of narrower hydrocarbon cuts (for example $C_5$ or $C_6$), in addition to the tert.-olefines the saturated and olefinic hydrocarbons and the gum-forming constituents, chiefly in the region of the C number of this cut, are also to be found.

Such hydrocarbon mixtures with various C atoms numbers and different degrees of unsaturation and with a content of tert.-olefines are available in petrochemical plants or refineries. These hydrocarbon mixtures can be obtained, for example, in the reaction of naphtha, liquid petroleum gas (LPG), crude oil distillates, gas oil or other starting hydrocarbon mixtures in steam crackers, catalytic crackers or isomerization or dehydrogenation plants. They can be employed according to the invention as such with a relatively wide range of C atom numbers, or as narrower cuts, which essentially contain, for example, $C_5$-hydrocarbons or $C_6$-hydrocarbons with only small amounts of the adjacent homologs. Typical compositions of $C_5$ cuts from steam crackers or catalytic crackers are, for example, as follows:

| Substance, % by weight (approximate) | Steam cracker | Catalytic cracker |
| --- | --- | --- |
| $C_4$/lights | 1–5 | 1–5 |
| n-/i-pentane | 20–30 | 30–35 |
| n-pentenes | 15–20 | 25–30 |
| 3-methyl-but-1-ene | 0.5–3 | 0.5–2 |
| 2-methyl-but-1-ene | 5–10 | 7–11 |
| 2-methyl-but-2-ene | 8–17 | 15–20 |
| cyclopentane | 4–6 | 1–3 |
| cyclopentene | 20–27 | 2–5 |
| diolefines/acetylenes | 0.5–5 | 0.5–5 |

Examples of alkanols which may be mentioned for the preparation of fuel components according to the invention are primary or secondary, preferably primary, alkanols with 1 to 8 C atoms, preferably 1 to 4 and particularly preferably 1 to 2 C atoms. The use of methanol is especially preferred. The alkanols are employed in the amount of 0.7 to 4 moles of alkanol/mole of total amount of tert. Olefins in the crude hydrocarbon mixture; a ratio of 0.8 to 2.5:1 is preferred, and a ratio of 1 to 2:1 is particularly preferred.

Hydrogen is employed in an amount which is at least equimolar to the total amount of gum-forming constituents, for example in an amount of 1 to 2 moles of $H_2$/mole of gum-forming constituents, preferably 1 to 1.2 moles/mole. Hydrogen can be employed in the pure or technical grade form. A hydrogen accompanied by $CH_4$ and/or $N_2$ which is obtained in petrochemical plants may be economically advantageous. The amount of $H_2$ in such pure or technical grade hydrogens is 70 to 100% of $H_2$, and is frequently about 80 to 90% of $H_2$-containing residual gases from petrochemical plants.

The process for preparing the fuel components according to the invention is carried out in the presence of a macroporous or gelatinous acid cation exchanger in the $H^+$ form with a degree of crosslinking of 2 to 65%, preferably 8 to 25%, and a specific surface area of 5 to 750 $m^2/g$, preferably 50 to 250 $m^2/g$ of dry exchanger resin, which is charged with one or more of the metals, in elemental form, designated below. Macroporous or gelatinous acid cation exchangers are known to the expert and can be prepared for example, by copolymerization of vinyl monomers and divinyl crosslinking agents, if appropriate, in the presence of solvents, or by condensation of phenol and formaldehyde.

Examples of vinyl monomers are styrene or acrylic acid esters; the divinyl crosslinking agent is, for example, divinylbenzene. Acid groups of such cation exchangers are, for example, carboxyl groups, phosphonic acid groups or sulphonic acid groups. Strongly acid styrene/divinylbenzene polymers which contain sulphonic acid groups and are commercially available under various names are preferably employed.

The mean pore radius of the cation exchangers can vary, for example, within the limits from 50 to 1,200 Å, preferably 70 to 500 Å. Such cation exchangers can have, for example, particle sizes of 0.1 to 2 mm, as bead polymers, or particle sizes of 10 to 100 μm, as powdered resins.

The cation exchangers are employed in the H+ form, after they have been charged with 0.001 to 10 g, preferably 0.2 to 3 g, per 1 g of dry cation exchanger, of one or more metals of sub-group VI and/or VII and/or VIII of the periodic table of the elements (Mendelejev) in elemental form. Examples of such metals which may be mentioned are: chromium, molybdenum, tungsten, manganese, rhenium, iron, cobalt, nickel, ruthenium, rhodium, palladium, osmium, iridium and platinum. Metals which are preferred are palladium, platinum, rhenium, molybdenum or nickel, and palladium, platinum and nickel are especially preferred. Preferably, furthermore, in each case only one of the metals mentioned is employed.

The cation exchangers can be charged with one or more of the metals mentioned by a procedure in which, for example, a non-complex, cationic salt of these metals is brought together with the cation exchanger in the H+ form in a manner which is known per se. If appropriate, the acid thereby liberated is neutralized by suitable compounds with an alkaline reaction, for example alkali metal hydroxide solutions. The amount of metal salt to be applied is calculated or determined by simple preliminary experiments, so that the desired amount of metal is applied in elemental form to the cation exchanger.

The cation exchanger doped with metal is washed neutral, dried, for example at 80° to 100° C. in vacuo, and then treated with hydrogen, for example under 2 to 50 bar, preferably 20 to 30 bar, at a temperature of 50° to 140° C., preferably 80° to 120° C., to convert the metals applied into the elemental state. In principle, it is also possible to use other reducing agents, such as hydrazine or formaldehyde.

The cation exchanger doped with metal is subjected to a load of 0.1 to 100, preferably 0.3 to 20 and particularly preferably 0.5 to 5 kg of crude hydrocarbon mixture, containing tert olefins per kg of cation exchanger per hour.

The process for preparing the fuel components according to the invention is carried out at temperature of 30° to 140° C., preferably 35° to 110° C. and particularly preferably 40° to 90° C. A pressure at which the reaction mixture, with the exception of the undissolved H₂, is at least partly liquid is established here. The relationship between the operating temperature chosen and such a pressure to be established is familiar to the expert.

The process for preparing the fuel components according to the invention can be carried out, for example, as follows, reference being made to the accompanying drawing:

The crude hydrocarbon mixture (6), the alkanol(s) (7) and H₂ (8) as the feedstock streams, after flowing through the preheater (3), are passed to the reactor (1) with the cation exchanger charged with metal and are reacted there. After leaving (1), the reaction mixture passes to the stabilization column (2), in which the residual gas, for example excess hydrogen and any CH₄ or N₂ present, is taken off over the top as stream (9). In the condenser (4), condensable substances are passed back to (2). (2) is heated by a circulatory heater (5). Some of the circulating bottom product is taken off as gum-free fuel component (10) containing alkyl tert.-alkyl ethers.

The fuel components according to the invention are characterized by a content of alkyl tert.-alkyl ethers which increase the octane rating. For example, a C₅ cut, reacted to fuel components according to the invention, from a steam cracker or catalytic cracker contains tert.-amyl methyl ether (TAME) if the reaction has been carried out with methanol. The degree of increase in the octane rating of course depends, in a manner familiar to the expert, on the amount of etherified tert.-olefines. Another advantage of the fuel components according to the invention is the desirable reduction in sensitivity, that is to say the reduction in the interval between the motor octane number (MON) and the research octane number (RON) and the improvement of their color numbers.

At a content of olefins which can be etherified of, for example, 10 to 30% by weight, a content of alkyl tert.-alkyl ethers of approximately 12 to 42% by weight in the fuel components can be reached.

The sensitivity is reduced from approximately 18 to 20 to approximately 13 to 15; and the color number (ASTM D1209) is regularly below 10, and can reach figures below 5.

In particular, the fuel components according to the invention contain only few gum-forming constituents so that the amount of gum is reliably within and below the maximum amount of gum (as the evaporation residue) of 5 mg/100 ml fuel components specified in DIN 51607 and DIN 51600 or in the ASTM standard for automotive gasoline.

The life-time of the cation exchanger is furthermore considerably lengthened by the addition of hydrogen in the process for preparing the inventive fuel components and by the gum formation thus prevented. This life-time is, for example, about 8 months without the addition of H₂ and at least 2 years with the addition of H₂.

The inventive gum-free fuel components, containing alkyl tert.-alkyl ethers can of course, if desired, be separated by distillation in a manner known to the expert, for example, in order to feed the portions of fuel components thereby obtainable separately and in a controlled manner to other fuels or other uses. For example, the following contents of the fuel components according to the invention could be removed in such a separation by distillation: the residual gas and unreacted hydrocarbons as the overhead stream; the main component alkyl tert.-alkyl ethers (for example TAME from a C₅ cut); a gum-free bottom stream containing higher ethers and other high-boiling constituents.

The following examples illustrate the invention without limiting it.

EXAMPLE 1

Preparation of a Cation Exchanger to be Employed According to the Invention.

Palladium acetate was made available to the commercially available cation exchanger "LEWATIT SPC 118" (styrene/divinyl copolymer with sulphonic acid groups from Bayer AG) in the water-moist H+ form in an amount such that, after reduction with H₂, one g of Pd per liter of dry resin was present on the cation exchanger. The acid liberated during the treatment with palladium acetate was neutralised with 1% strength by weight NaOH. The cation exchanger was washed neutral and dried at 100° C. under the vacuum of a waterpump for 24 hours. The palladium on the cation exchanger was reduced to the metal at 90° to 100° C.

under an H$_2$ pressure of 20 to 25 bar in the course of 48 hours.

EXAMPLE 2

The cation exchanger obtained according to Example 1 was introduced into a flow reactor which was capable of being heated and had an internal diameter of 20 mm and temperature-measuring points at intervals of in each case 100 mm. The C$_5$ stream of a steam cracker (so-called aromatic forerunning) containing 14.5% by weight of 2-methylbut-2-ene, 3.8% by weight of 2-methylbut-1-ene and 0.5% by weight of 3-methylbut-1-ene was employed as the crude hydrocarbon mixture. This substance stream had a MON of 76 and a RON of 91 and a boiling range of 35° to 65° C. The load on the cation exchanger charged with Pd was set at a load of 1 and the pressure was set at 10 bar; the temperature was kept between 70° and 75° C. The hydrocarbon mixture was mixed with the stoichiometric amount of methanol (based on the tert.-amylenes) in a mixing chamber upstream of the reactor and prewarmed. The amount of hydrogen added was adjusted so that the gas load on the cation exchanger was 80 liter of H$_2$ per liter of cation exchanger per hour. A colourless fuel component containing 17.6% by weight of TAME was obtained as the reaction product. This fuel component, had an evaporation residue of 1 mg/100 ml, a color number (ASTM D1209) of <5, a MON (clear) of 80 and a RON (clear) of 93.

EXAMPLE 3

The experiment was carried out as in Example 2, but without the addition of H$_2$. The reaction product, which also contained 17.5% by weight of TAME, is, however, yellow-colored and has a color number (ASTM D1209) of about 3,000 and an evaporation residue of 21 mg/100 ml. The octane rating was similar to those from experiment 2.

It will be appreciated that the instant specification and claims are set forth by way of illustration and not limitation, and that various modifications and changes may be made without departing from the spirit and scope of the present invention.

What is claimed is:

1. A process to prepare a gum-free fuel containing alkyl tert.-alkyl ethers, comprising reacting (1) a crude hydrocarbon mixture containing straight-chain and/or branched and/or cyclic saturated and monounsaturated hydrocarbons with 5 to 8 carbon atoms and small amounts of adjacent homologs and furthermore containing gum-forming constituents and containing one or more tert.-olefins, simultaneously with (2) one or more alkanols and (3) hydrogen, the crude hydrocarbon mixture, the alkanols, and the hydrogen being taken from separate feedstock streams, to form a reaction mixture on a macroporous or gelatinous cation exchanger in the H+ form, the cation exchanger comprising 0.001 to 10 g of one or more metals of sub-group VI and/or VII and/or VIII of the periodic table of the elements in elemental form per liter of dry cation exchanger and with a degree of crosslinking of 2 to 65% and a specific surface area of 5 to 750 m$^2$/g of dry exchanger resin, in the liquid phase at 30° C. to 140° C., wherein the hydrogen is employed in an amount of 1 to 2 moles per mole of the total amount of gum-forming constituents and wherein the gum-forming constituents are present in the crude hydrocarbon mixture in an amount of about 0.5 to 5% by weight.

2. A process according to claim 1, wherein the metal is selected from the group consisting of palladium, platinum, rhenium, molybdenum, nickel and mixtures thereof.

3. A process according to claim 2, wherein the metal is selected from the group consisting of palladium, platinum and nickel.

4. A process according to claim 1, wherein the reaction is carried out under a load on the cation exchanger of 0.1 to 100 kg of the crude hydrocarbon mixture per kg of the cation exchanger per hour.

5. A process according to claim 1, wherein the reaction is carried out under a load on the cation exchanger of 0.3 to 20 kg of the crude hydrocarbon mixture per kg of cation exchanger per hour.

6. A process according to claim 1, wherein the reaction is carried out under a load on the cation exchanger of 0.5 to 5 kg of the crude hydrocarbon mixture per kg of cation exchanger per hour.

7. A process according to claim 1, wherein the hydrogen is employed in am amount of 1 to 1.2 moles per mole of the total amount of gum-forming constituents.

8. A process according to claim 1, wherein said hydrogen is technical grade hydrogen.

9. A process according to claim 1, wherein the reaction mixture is present at least partly in the liquid phase, with the exception of undissolved hydrogen.

10. A process according to claim 1, wherein the amount of alkanol is 0.7 to 4 moles per mole of the total amount of tert.-olefin.

11. A process according to claim 1, wherein the amount of alkanol is 0.8 to 2.5 moles per mole of the total amount of tert.-olefin.

12. A process according to claim 1, wherein the amount of alkanol is 1 to 2 moles per mole of the total amount of tert.-olefin.

13. A process according to claim 1, wherein the alkanol is a primary or secondary alkanol with 1 to 8 carbon atoms.

14. A process according to claim 1, wherein the alkanol is a primary or secondary alkanol with 1 to 4 carbon atoms.

15. A process according to claim 1, wherein the alkanol is selected from the group consisting of methanol and ethanol.

16. A process according to claim 1, wherein the degree of crosslinking of the cation exchanger is 8 to 25%.

17. A process according to claim 1, wherein said specific surface area is 50 to 250 m$^2$/g of dry exchanger resin.

18. A process according to claim 1, wherein the mean pore radius of the cation exchanger is 50 to 1,200 Å.

19. A process according to claim 1, wherein the cation exchange is charged with 0.2 to 3 g of said metal per 1 liter of dry cation exchanger.

* * * * *

UNITED STATES PATENT AND TRADEMARK OFFICE
CERTIFICATE OF CORRECTION

PATENT NO. : 5,084,070

DATED : January 28, 1992

INVENTOR(S) : Kohler et al.

It is certified that error appears in the above-identified patent and that said Letters Patent is hereby corrected as shown below:

Title Page      ABSTRACT: Next to last line delete " element in element " and substitute -- elements in elemental --

Signed and Sealed this

Tenth Day of August, 1993

Attest:

MICHAEL K. KIRK

*Attesting Officer*      *Acting Commissioner of Patents and Trademarks*